US010292906B1

(12) United States Patent
Gershoni et al.

(10) Patent No.: US 10,292,906 B1
(45) Date of Patent: May 21, 2019

(54) CONTACTLESS AUTOMATIC PILL DISPENSER WITH BLISTER-PACK SUPPORT

(71) Applicants: Daniel Gershoni, Weston, FL (US); Farhad David Nosrati, Encino, CA (US)

(72) Inventors: Daniel Gershoni, Weston, FL (US); Farhad David Nosrati, Encino, CA (US)

( * ) Notice: Subject to any disclaimer, the term of this patent is extended or adjusted under 35 U.S.C. 154(b) by 1 day.

(21) Appl. No.: 15/627,443

(22) Filed: Jun. 20, 2017

Related U.S. Application Data

(60) Provisional application No. 62/352,641, filed on Jun. 21, 2016.

(51) Int. Cl.
| | |
|---|---|
| *A61J 7/04* | (2006.01) |
| *G06F 19/00* | (2018.01) |
| *G07F 11/54* | (2006.01) |
| *B65D 83/04* | (2006.01) |
| *A61J 1/03* | (2006.01) |

(52) U.S. Cl.
CPC ............. *A61J 7/0481* (2013.01); *A61J 1/035* (2013.01); *A61J 7/0418* (2015.05); *A61J 7/0427* (2015.05); *B65D 83/0454* (2013.01); *G06F 19/3462* (2013.01); *G07F 11/54* (2013.01); *A61J 2200/30* (2013.01); *A61J 2205/60* (2013.01); *A61J 2205/70* (2013.01)

(58) Field of Classification Search
CPC .. A61J 1/035; G07F 17/0092; B65D 83/0463; B65D 83/0454

USPC .................................................. 700/231–244
See application file for complete search history.

(56) References Cited

U.S. PATENT DOCUMENTS

| | | | | |
|---|---|---|---|---|
| 4,015,717 A | * | 4/1977 | Richardson | A61J 7/04 206/531 |
| 5,047,948 A | * | 9/1991 | Turner | A61J 7/0084 221/15 |
| 5,348,158 A | | 9/1994 | Honan et al. | |
| 5,685,435 A | * | 11/1997 | Picioccio | B67D 3/00 209/677 |
| 5,988,429 A | | 11/1999 | Coe | |
| 6,415,202 B1 | * | 7/2002 | Halfacre | A61J 7/0481 221/102 |
| 6,471,087 B1 | * | 10/2002 | Shusterman | A61B 5/02055 221/2 |
| 6,651,840 B1 | | 11/2003 | Van Dullemen et al. | |
| 7,108,153 B2 | * | 9/2006 | Wood | A61J 7/0076 221/105 |

(Continued)

*Primary Examiner* — Timothy R Waggoner

(57) ABSTRACT

An apparatus for dispensing pills comprising a pill storage section, a dispensing section located at a lower end of the storage section, an optical sensor, a memory, controller and wireless communication module and a supporting tray for one ring-shaped blister pack. A spring loaded lever is provided as push-out means in line with the respective pills of the blister pack and with the passage opening and can be operated for pushing out the pills to be dispensed through the passage opening. A motorized mechanism is provided as means for rotatable positioning of the blister pack stepwise relative to the part of the apparatus including the push-out means. Optical sensor detects presence of an object such as a person's hand at the passage opening and allows the pills to be dispensed automatically.

11 Claims, 19 Drawing Sheets

(56) References Cited

U.S. PATENT DOCUMENTS

| | | | |
|---|---|---|---|
| 7,602,275 B2 * | 10/2009 | Dishongh | A61J 7/0481 |
| | | | 340/309.16 |
| 7,946,488 B2 | 5/2011 | Madey | |
| 8,548,623 B2 * | 10/2013 | Poutiatine | A61J 7/0053 |
| | | | 700/236 |
| 8,670,865 B2 | 3/2014 | Coe | |
| 9,211,233 B2 | 12/2015 | Shavelsky et al. | |
| 9,539,177 B2 * | 1/2017 | Solvell | A61J 7/0076 |
| 2004/0129716 A1 * | 7/2004 | Naufel | G07F 11/62 |
| | | | 221/9 |
| 2015/0137972 A1 * | 5/2015 | Nepo | G08B 25/016 |
| | | | 340/539.13 |

\* cited by examiner

CONTACTLESS AUTOMATIC PILL DISPENSER WITH BLISTER-PACK SUPPORT

CROSS-REFERENCE TO RELATED APPLICATIONS

This application takes priority from provisional application Ser. No. 62/352,641 filed on Jun. 21, 2016.

BACKGROUND OF INVENTION

1. Field of the Invention

The present invention relates to a medication dispenser configured to remind a user to take medication and dispense medication to a user, and provide a system for tracking medication compliance. The present invention further relates to a pill dispenser for dispensing a pill or plurality of pills from a blister pack to a collector. The present invention further relates to a medication dispenser utilizing optical sensors to detect objects within close proximity of the device and automatically dispense medicine without requiring any physical contact. The present invention further relates to a medication dispenser utilizing a unique motorized punching mechanism to dispense pills contained in a sealed blister package.

2. Description of Prior Art

A variety of products and techniques for reminding patients to take their medications, as prescribed, are known. Patients frequently exhibit poor patient compliance in properly following through a particular drug regimen. Some compliance intervention systems offered by health care providers are designed to remind the patient to take the medication and alert a remote caregiver if the patient does not comply with taking the medication as prescribed. Some of these compliance intervention systems include sensors/reminders in the home, a network connection, and outbound messaging to a caregiver or even back to the patient. However, such systems are generally limited or very specific to a medication type.

In order to avoid the potential for mishaps when dispensing pills from a container, pharmaceutical suppliers have developed blister pack compartments designed to hold a single dose of medication. Such packages permit the handling of only a single dose of medicine at a time. The blister pack comprises a sheet of plastic having an array of spaced apart blisters protruding from an obverse surface of the sheet. Each blister is open to a reverse surface of the sheet and serves as a separate compartment. A single pill is deposited in each compartment and a sheet of metal foil is affixed to the reverse surface of the sheet, closing the compartments, and separately sealing each pill. When a pill is needed, a patient may select a particular compartment, press the blister to collapse the compartment, rupturing the foil, and releasing the pill. Unused pills remain sealed in the compartments of the blister pack, until they are removed for use. The blister pack avoids the potential for spilling a number of pills during the process of removing a single dose of medication. In addition, the blister pack facilitates tracking the number of pills previously administered, because a patient may count the number of opened compartments. Also, sanitary conditions are improved because the supply of pills is not repeatedly handled.

Unfortunately, the process of pressing a compartment and retrieving a pill as it passes through the foil on the reverse side of the blister pack is difficult, particularly for elderly patients, who may have impaired vision and reduced manual dexterity. There is a need for a device, which can dispense a pill from a blister pack reliably and which can deposit the pill into a collector from which the pill may be easily retrieved. There is a need for a pill dispenser, which is compact and manually operated, to deliver a single pill or plurality of pills from a blister pack to a collector.

Furthermore, medication in solid form such as tablets, pills, capsules and the like are sometimes dispensed to patients in dispensers having blister packages, which include individually sealed blisters. A common deficiency of many schemes that try to incorporate a blister pack is that they can't also accommodate dispensing additional medications that are presented in non-blister pack forms.

Furthermore, in most cases, patients take daily supplemental such as vitamins along with their regularly prescribed medications. Prior arts do not support a mechanism for automatically dispensing both manually stored (and filled) medications (such as vitamins) along with the medications contained in pre-sealed containers such as blister-packs.

Furthermore, prior art medication dispensers require the user to make physical contact with the device in order to dispense the medication, such as pressing a button, pushing a lever, opening an enclosure, opening a container cap or door and so on. What is needed is a device that dispenses medication automatically when a patient, care giver, operator, or authorized user is either within close proximity of the device or places their hand or a small container underneath or within close proximity of the dispensing device.

Furthermore, in case of a missed medication event, prior art devices are limited in how they notify the patient when he or she forgets or otherwise fails to take the medication as scheduled. To be notified, a patient typically has to be nearby the device to hear a message or alarm sound, for example. They do not provide a wireless notification device such as Personal Emergency Management System or PERS that the user can carry around with them, even when they are far from the medication dispensing device, which using wireless communications can receive alerts from the medication dispensing devoice and notify the person.

The present invention improves prior systems and overcomes the prior systems' deficiencies in a unique and novel manner as disclosed herein.

SUMMARY OF THE INVENTION

In one aspect of the invention, the apparatus comprises a medication dispenser configured to remind a user, dispense medication to a user, and provide a system for tracking medication compliance.

Another feature of the present invention further relates to a pill dispenser for dispensing a pill or plurality of pills from a pre-sealed container such as a blister pack to a collector.

Another feature of the present invention is that multiple dispensing mechanisms are provided. In one embodiment of the present invention, there is provided a Manual Push Lever (MPL) that the user can press down to puncture the sealed container such as the blister pack and dispenses the pills. In another aspect of the dispensing mechanism of the current invention, there is a novel Dual Press Solenoid Lever (DPSL) to puncture the sealed container such as the blister pack and dispense the pills. In yet another embodiment of the dispensing mechanism of the current invention, there is provided a novel Dual Press Motorized Lever (DPML) to puncture the sealed container such as the blister pack and dispense the pills.

Another feature of the present invention relates to a pill dispenser capable of simultaneously dispensing pills from a Manual Tray and from a sealed container such as a Blister-Pack unit. This novel concept allows users the flexibility to add additional medications such vitamin pills to their regular medication dosage at one or more intervals during each day.

Another feature of the present invention includes one or more optical sensors placed at the push out passage opening that can detect when an object such as human hand is placed under the exit compartment, triggering a motorized mechanism to rotate the circular tray containing the medications and to position the next dosage of pills at the passage opening to be dispensed. The optical sensors may also serve as a barcode scanner for scanning medication labels to assist with the verification and adherence process. Barcode scanning process can also be achieved by connecting the device to an external barcode scanner via one of the available communication ports of USB, Bluetooth or WiFi.

The present invention further includes the feature of a wireless Near Field Communication (NFC) to detect and authenticate the presence of the authorized user before allowing for the medications to be dispensed.

The present invention further includes a display unit that provides various information on the medications to be taken, including but not limited to reminder messages, instructions on the medications and how to take them, as well as actual images of the medications related to each dose of medication. Furthermore, various images and recorded instructional videos also may be displayed. In one embodiment of the current invention, a tablet computing device is utilized to provide the user interface functionality and the display module requirement.

The present invention further includes a unique locking mechanism to assist with the adherence process.

The locking mechanism of the present invention may be further equipped with series of electronic sensors that detect tampering with the device. In case tampering occurs, the present invention will enter into a special, restricted Alert Mode and notify the user via audible alarms as well as notifying the remote operators and caregivers utilizing the built-in Wireless module.

Once the present invention device has entered into an Alert Mode, a series of electronic alert signals and messages are sent to remote operators, computing devices and mobile devices using various wireless communications methods including but not limited to Bluetooth, WiFi, 2G, 3G and 4G and 5G, and the like. Furthermore, utilizing the wireless extension device PERS being carried by the patient on their body, the patient can be notified of the alert status.

The present invention further includes a button for a unique Early Dose dispensing feature. The present invention can be pre-programmed to allow one or more early dosages of the medication to be dispensed.

The present invention may further include biometrics sensors such as fingerprint scanners, retina scanners, and the like, for secure access to the device, as well as secure Early Dose operation.

The present invention may further include a camera, microphone and speaker set to allow live audio and video communication with care givers, physicians and remote call center operators, and for audio and video communication to operate the dispenser of the present invention.

The present invention may further include a feature of a sensing mechanism to detect a user approaching the device and illuminate a light panel when they are within close proximity of the device. This sensing mechanism may also activate any of the other features of the present invention.

The present invention may further include the feature of a sensing mechanism to illuminate a light panel when the device is touched by a user.

In yet another configuration, the present invention can be made waterproof.

The present invention may further include a built-in thermometer with user contact points for measuring body temperature. The display unit provides the temperature reading locally, while wireless communication module will transmit that information to remote operator and caregivers via Bluetooth, WiFi, 2G, 3G, 4G, 5G and other communication means.

The present invention may further include the feature of a barcode scanner for scanning medication labels to assist with the verification and adherence process. Barcode scanning process can also be achieved by connecting the device of the present invention to an external barcode scanner via one of the available communication ports of USB, Bluetooth or WiFi.

The present invention may further includes a scale for measuring various liquid medication dosages and displaying the weight of the liquid medication dose being taken, as well as the weight of the liquid medication bottle before and after the consumption of the said medicine. The scale feature of the present invention may also be used for other purposes, including, but not limited to, weighing the before and after of dry medications to assist with medication adherence process.

The present invention further includes a feature of a spring loaded lever to be utilized as a push-out means in line with the respective pills of the blister pack to protrude each individual blister compartment and push out the pills contained within that compartment onto the bottom release tray.

The present invention may further include a unique and novel, remote Personal Emergency Reporting System (PERS) to be used to alert remote computing systems, mobile devices, operators and caregivers when needed. The present invention can maintain remote contact with the PERS unit wirelessly to alert the user of the status of his or her medication adherence status.

The present invention further includes a unique Check-On-Me feature, also referred to as the I-Check, that comprises a button that when pressed, will communicate wirelessly with outside computers, mobile devices and remote caregivers and operators by sending various electronic signals, messages to outside computers, mobile devices and remote operators to alert them of the status of the user. The present invention can then establish a 2-way voice communications with remote operator both directly as well as through the PERS device. Caregivers and remote operator can program the present invention with various time daily as well as weekly times for enquiring about the status and well-being of the user. The user will then be alerted at the said times via display messages as well as audio alarms to press the Check-On-Me button to provide feedback of their status. The allowable time window for the user to respond to a Check-On-Me alert can further be pre-programmed by the caregiver and remote operators.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

It should be noted that references to "an," "one," or "various" embodiments in this disclosure are not necessarily to the same embodiment, and such references contemplate more than one embodiment.

The present invention disclosed herein is Contactless Automatic Pill Dispenser configured to remind a user and dispense medication to a user, and provide a system for tracking medication compliance.

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current Good Manufacturing Practice guidelines.

As used herein the term "Computing Device" includes a desktop, laptop or tablet computer, as well as a mobile device or functionally similar device.

As used herein, the terms "patient," "care giver," "user," and the like all refer to the one who is using the present invention and are meant to be interchangeable and non-limiting.

"Telemetry" means the wireless transmission and reception of measured quantities for the purpose of remotely monitoring environmental conditions or equipment parameters.

"Software Application" means all the computer software that causes a computer to perform useful tasks beyond the running of the computer itself.

Disclosed herein and illustrated in FIGS. 1 through 19 is the present invention Contactless Automatic Pill Dispenser Device 100.

Figure 1:
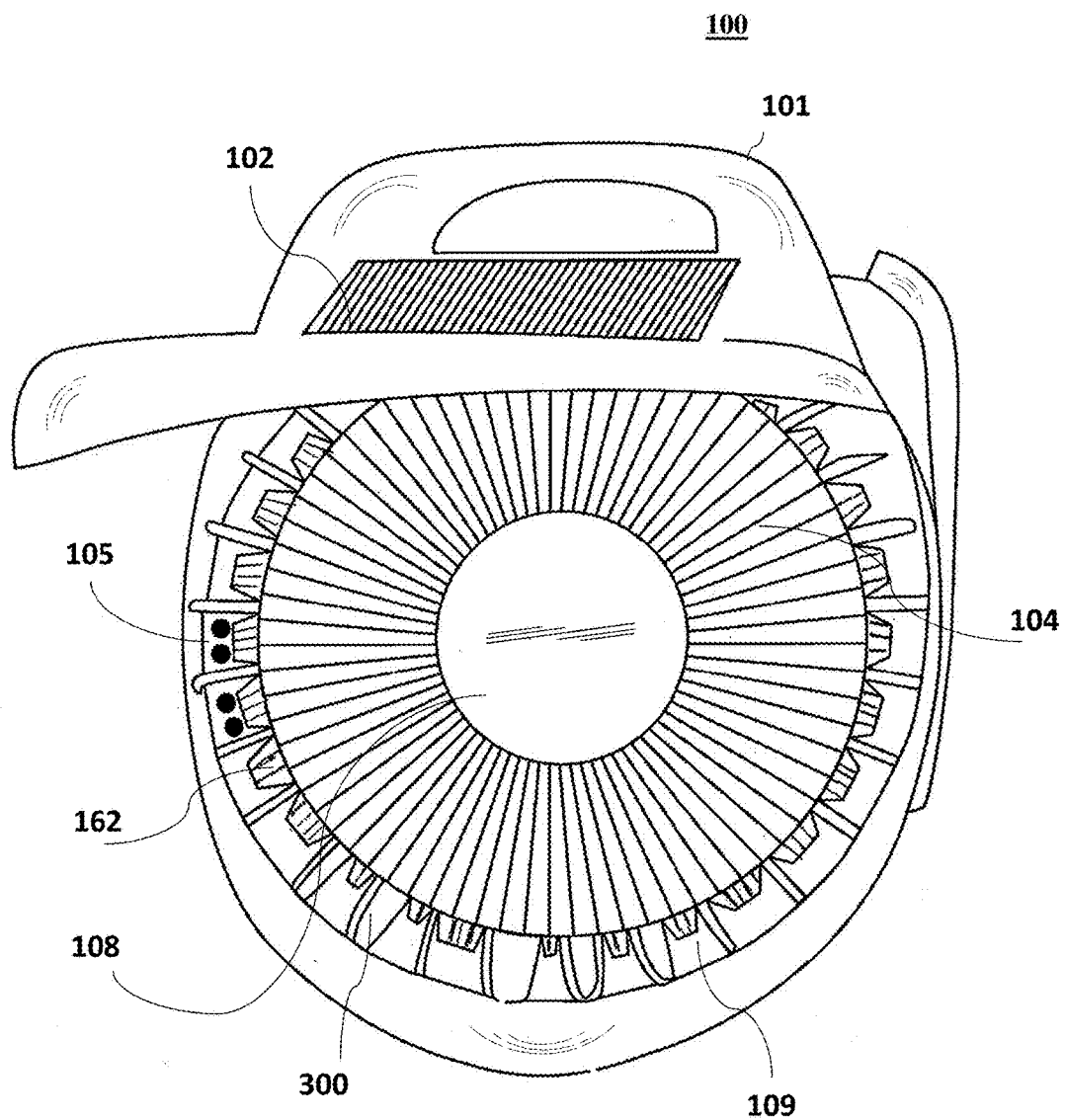
FIG. 1 is a top perspective view of a preferred embodiment of the present invention Contactless Automatic Pill Dispenser in its open position.
Figure 2:
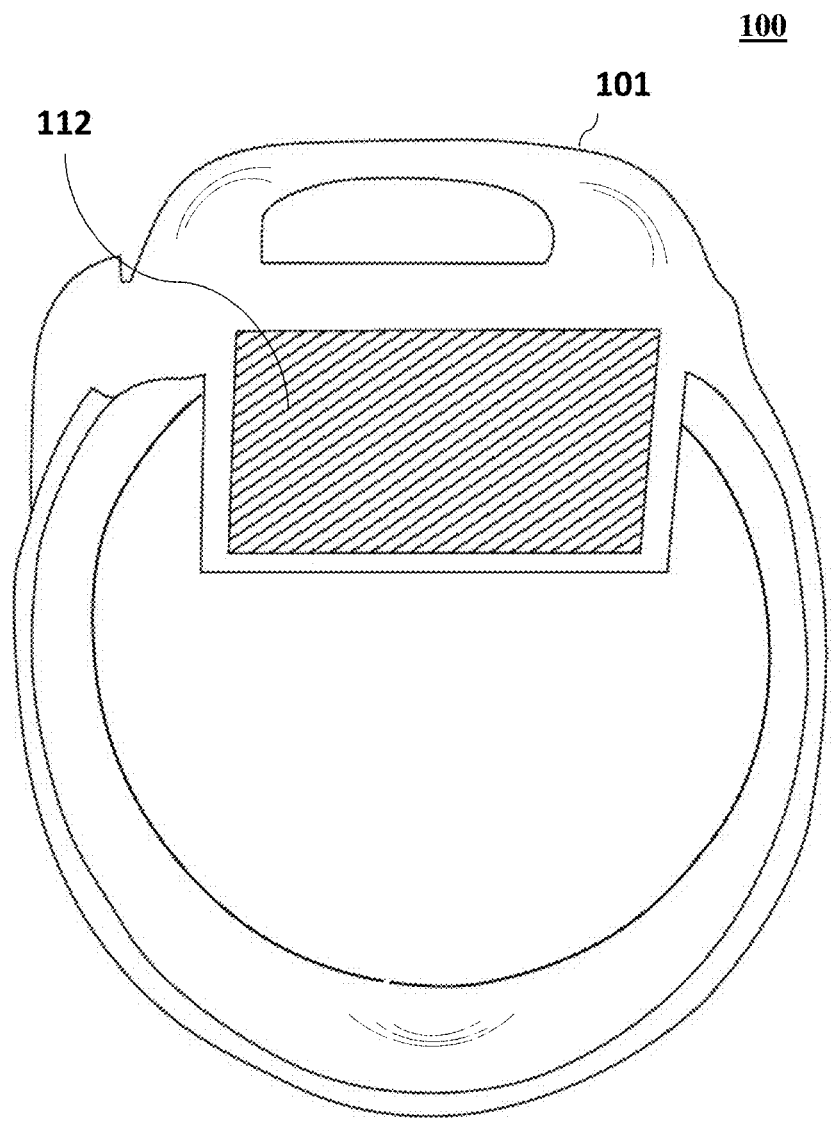
FIG. 2 is a top perspective view of the preferred embodiment of the present invention in its closed position.
Figure 3:
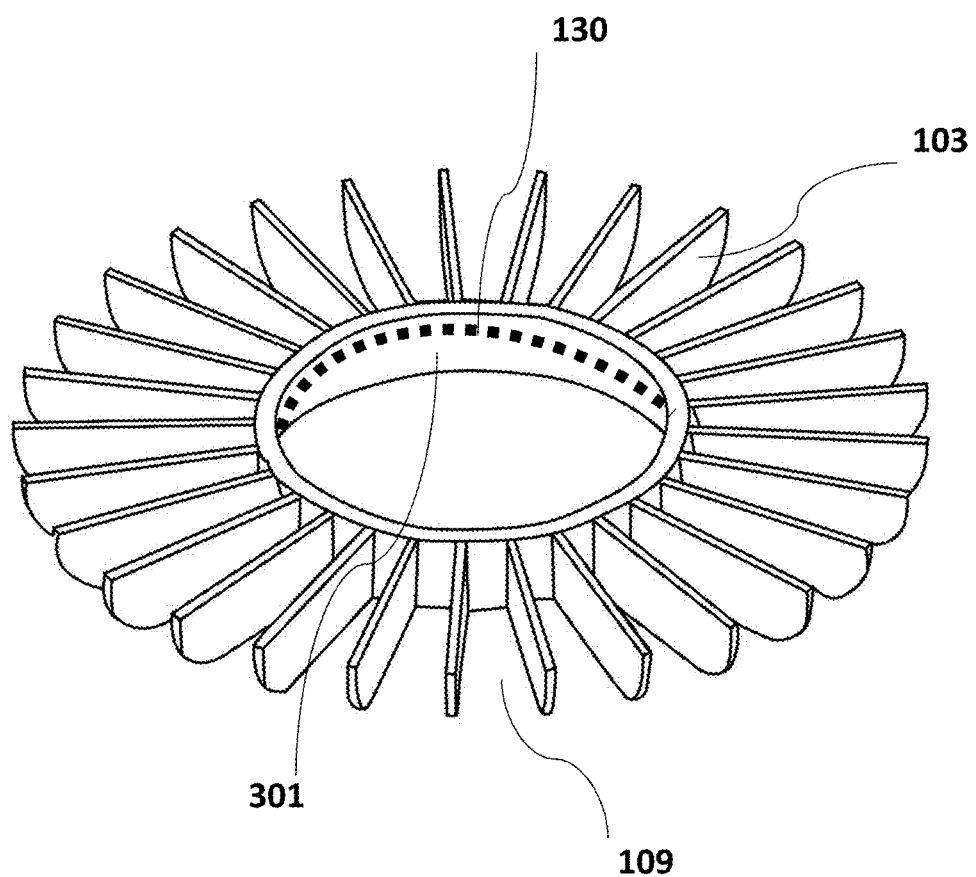
FIG. 3 is a top perspective view of a carousel tray of the preferred embodiment of the present invention.
Figure 4:
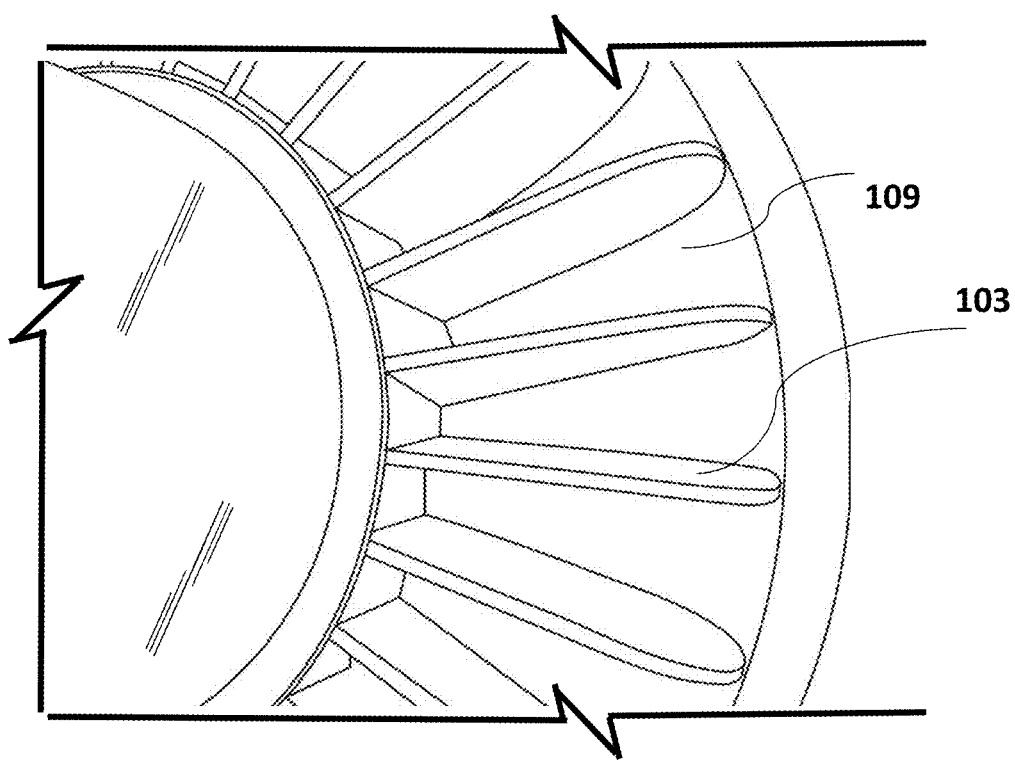
FIG. 4 is a detail view of the carousel tray within the housing of the preferred embodiment of the present invention in its open position showing the top tray compartment for blister-packs in a close-up.
Figure 5:
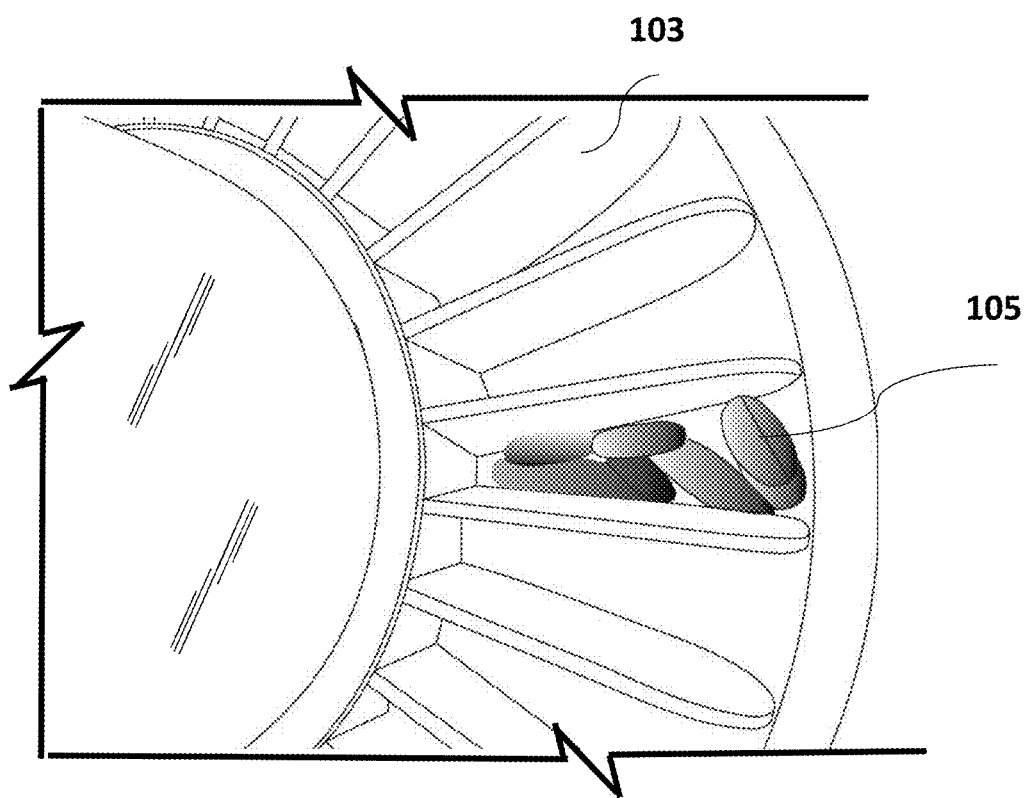
FIG. 5 is a detail view of the carousel tray containing manually placed medication within the housing of the preferred embodiment of the present invention.

As shown in FIGS. 1 and 2, the present invention dispenser 100, includes a top cover which may "open", as illustrated in FIG. 1, and may close, as illustrated in FIG. 2, wherein the dispenser 100 is generally round or circular in shape. The dispenser 100 may include a carrying handle 101 along the exterior of the dispenser 100. Within the dispenser 100 is a portable computing device 102. The computing device 102 may be either an embedded part of the current invention device, as well as a separate removable unit. There is also provided a round carousal tray 300, which is preferably "keyed" such that it is inserted in only one unique position. The round carousal tray 300 provides individual storage compartments 109 for storing manually placed pills 105 including but not limited to vitamin pills.

The present invention dispenser 100, further allows the insertion of a blister package 104 with one or more blister pockets 162 which can be pre-filled with additional medication including but not limited to pills and powder medication to be dispensed simultaneously along with manually loaded pills such as vitamins. Furthermore, the present invention dispenser 100 provides the unique ability for automatic and dual-dispensing of manually loaded pills along with the pre-filled medication in the blister-pack.

The present invention dispenser 100, further includes one or more compartments for work area 108 which houses the electro-mechanical control unit 150.

Figure 6:
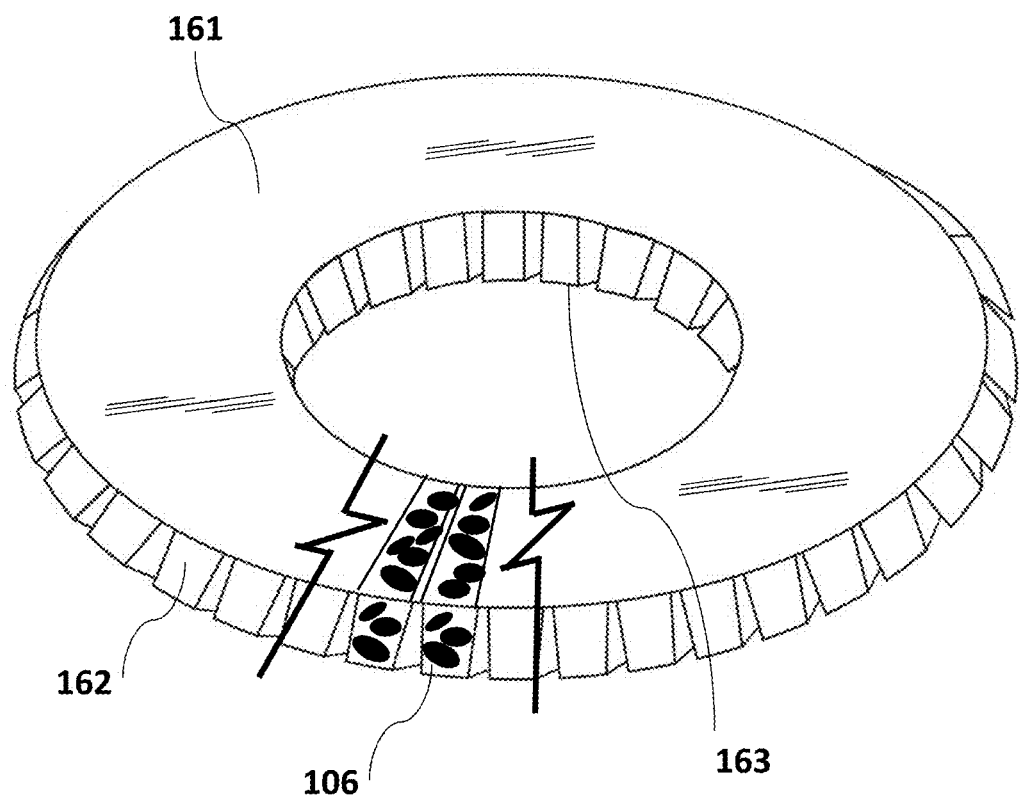
FIG. 6 is a top perspective view of a plaster-pack of the preferred embodiment of the present invention.

Referring now to FIGS. 3-6 and 10, Blister-pack 104 has a circular top 161 from which a multiplicity of pockets 162 depend. The pockets 162 are spaced apart along the underside of the circular top 161. The blister-pack 104 resides upon the carousal tray 300 such that pockets 162 fit within compartments 109. FIG. 6 additionally shows two of the pockets 162 in a transparent manner so that the medication 106 is visible within the blister-pack 104.

Blister-pack 104 may contain a supply of one or more medications 106 to be dispensed or may have an empty pocket 162 to coincide with the manually placed medication 105 in the compartment 109 below. It will be shown how the manual medication 105 and the blister-pack medication 106 are dispensed.

Dispenser 100 further contains one or more work areas compartments 108 wherein the electro-mechanical control unit 150 comprising of electronics, motors, cables and other functional parts reside. One such functional part of the present invention is the rotary motor 131 along with motor controller circuitry 121 which enables the carousel tray 300 to be activated and revolved at pre-designated times in order to allow dispensing of manual medication 105 and the blister pack medication 106 at specified times. Yet, another such functional part of the present invention is the dual punch motor 132 along with motor controller circuitry 122 which provides motorized movement of a lever in order to provide an automatic punching mechanism for puncturing the blister pack compartments 162, allowing medication stored in the blister pack to be released and dispensed. In addition, the electro-mechanical control unit 150 comprises of wireless module 140 containing the 2G, 3G, 4G and 5G electronics 141, Wi-Fi 142, Bluetooth 143 and RFID 144. Additionally, the electro-mechanical control unit 150 comprises of the User Interface unit 115 which may include an embedded display 112, buttons 120, speaker and microphone 119 as well as a separate portable computing device such as a tablet computer 102.

The electro-mechanical control unit 150 further comprises of a unique and novel rotary position sensing circuitry 130. A variable-load resistor 301 is placed along the in inner circular wall of the round carousal tray 300. As the round carousal try is enabled and rotates, the rotary position sensing circuitry 130 senses and measures the resistive load across the variable-load resistor 130 and computes the accurate position of the round carousal tray.

A medication egress 191 is located on the dispenser 100, preferably on the underside 350 or along the lower perimeter of the dispenser 360. Dispensing of the medication 105 and 106 is monitored and controlled via the electro-mechanical control unit 150 through the user interface 115 or through a corresponding app or web interface. Medication may also be dispensed by utilizing one or more optical or photo sensors 901.

Portable computing device 102, as previously discussed may be a computer chip 118 and memory 117, may be a tablet computer or a cell phone 102, and the like, and may be permanently or temporarily connected to the dispenser 100. In other words, computing device 102 may be embedded in the present invention or may be a separate, removable unit. the electro-mechanical control unit 150 further includes a power management unit 119 to monitor the battery usage and charging status.

User interface 115 may be provided thru the computing device 102 or may consist of a separate display 112, buttons 120 and speaker and microphone 119 units. User Interface 115 at least includes a feature that allows users to view their medication schedule, notification messages, various settings, as well as access to external medication databases including but not limited to FDA databases to guide users on their medication scheduling and usage guidance.

User interface 115 provides for the pre-programmed schedule for dispensing medications 105 and/or 106 at proper times based on the pre-programmed schedule. This schedule may be downloaded thru the wireless module 140 remotely or manually through the use of the User Interface module 115. User interface 115 is designed to allow simultaneous dispense medication from the blister-pack and from the manually placed medication and keep track of the pre-programmed schedule and time-table.

Figure 10:
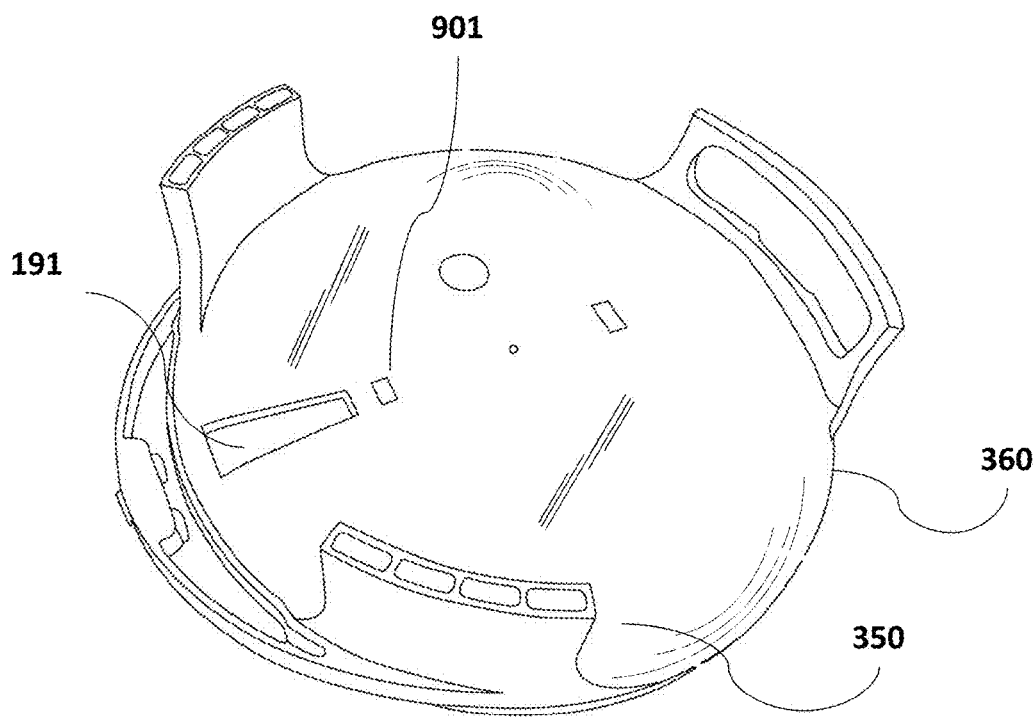
FIG. 10 is a bottom perspective of the alternate embodiment of the present invention.

As mentioned previously, the dispenser 100 of the present invention is motorized, allowing carousal tray 300 to activate and turn at pre-designated times in order to allow dispensing of medications 105 and/or 106 at proper times. As illustrated in FIG. 10, medications 105, 106 can be dispensed by the user via direct interface with the computing device 102 and also by utilizing one or more optical and/or photo sensors 901, which are capable of detecting when an object, such as the user's hand, has been placed under the medication egress 191.

Figure 7:
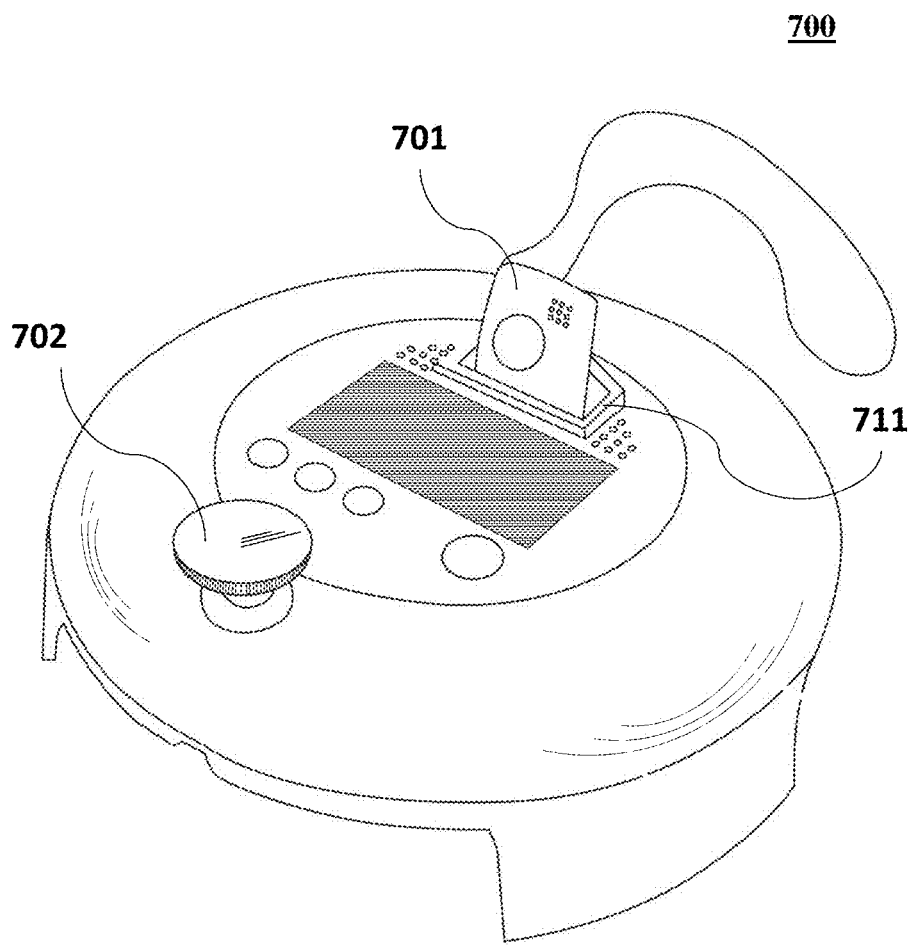
FIG. 7 is a top perspective view of an alternate embodiment of the present invention further illustrating an alternate embodiment of a manual dispenser lever and alternate embodiment of non-foldable legs.

Referring now to FIG. 7, there is shown a second embodiment of the present invention dispenser, wherein there is provided a Manual Push Lever (MPL) 702 to manually dispense the pills from the inserted sealed blister pack.

One of the unique and novel features of the present invention dispenser 100 is the ability to dual-dispense the medications 105, 106 by utilizing a motorized mechanism 131 to turn the carousal tray 300 to dispense manually loaded medication along with a manual push lever 702 for the user to further dispense the pills contained in corresponding pocket 162 of the blister pack 104.

FIG. 7 further shows the removable wireless Personal Emergency Response System (PERS) 701 that the user can carry with them to receive notifications on missed medications, medication schedules and the medication devise status. Dispenser 700 provides for a docking station 711 for the PERS 701 to be inserted and charged. Pill dispenser 700 also provides a wireless communication link 140 to the removable PERS 701, as shown in detail in FIG. 8, to communicate user status and alert notifications with the user at all times when away from the dispenser 700.

Figure 8:
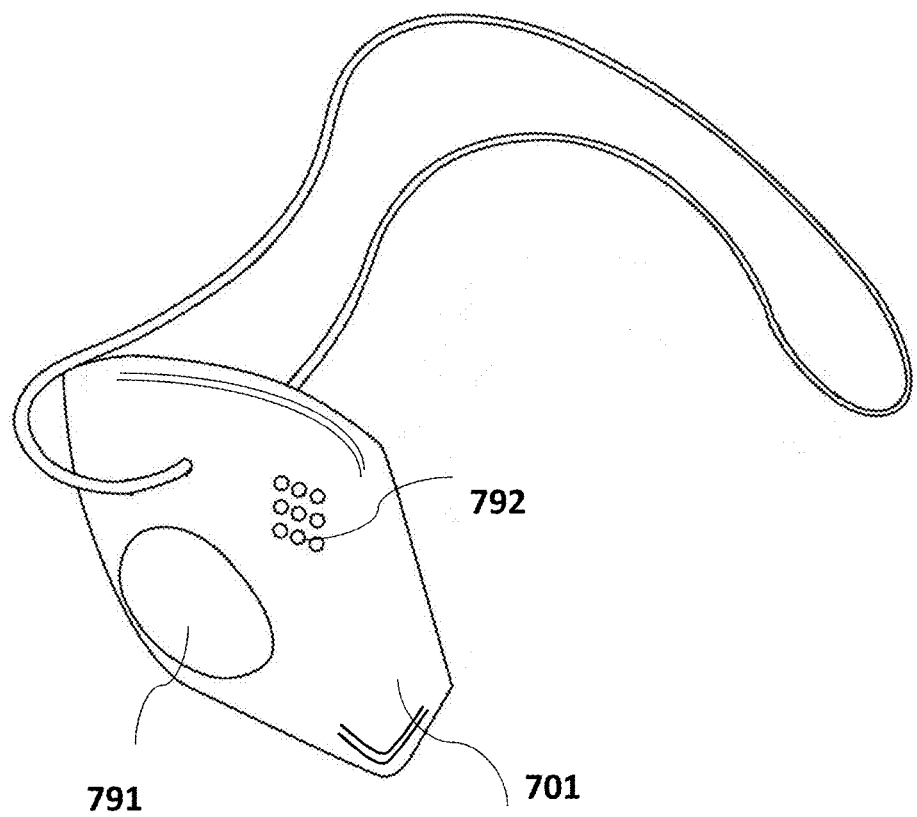
FIG. 8 is a personal removable remote emergency response button of the preferred embodiment of the present invention.

Now referring to FIG. 8, there is shown a detail of the PERS 701, which may be removable, as shown, or may be an integral part of the Dispenser 700. The PERS may include a button 791 and a speaker 792. Button 791 is to be pressed by the user when prompted. These prompts may be random, pre-determined, or a combination of both. If button 791 is not pressed after a pre-measured period of time after the prompt is given, a second prompt may occur or the device may go directly to its notification functions, as further illustrated in detail in FIG. 17. Speaker 792 may be a one-way speaker or a two-way speaker, thereby providing the prompt to touch the button 791 or, if two-way, to provide the user the ability to speak directly with a person or give commands to a semi-automated or fully automated system.

Figure 9:
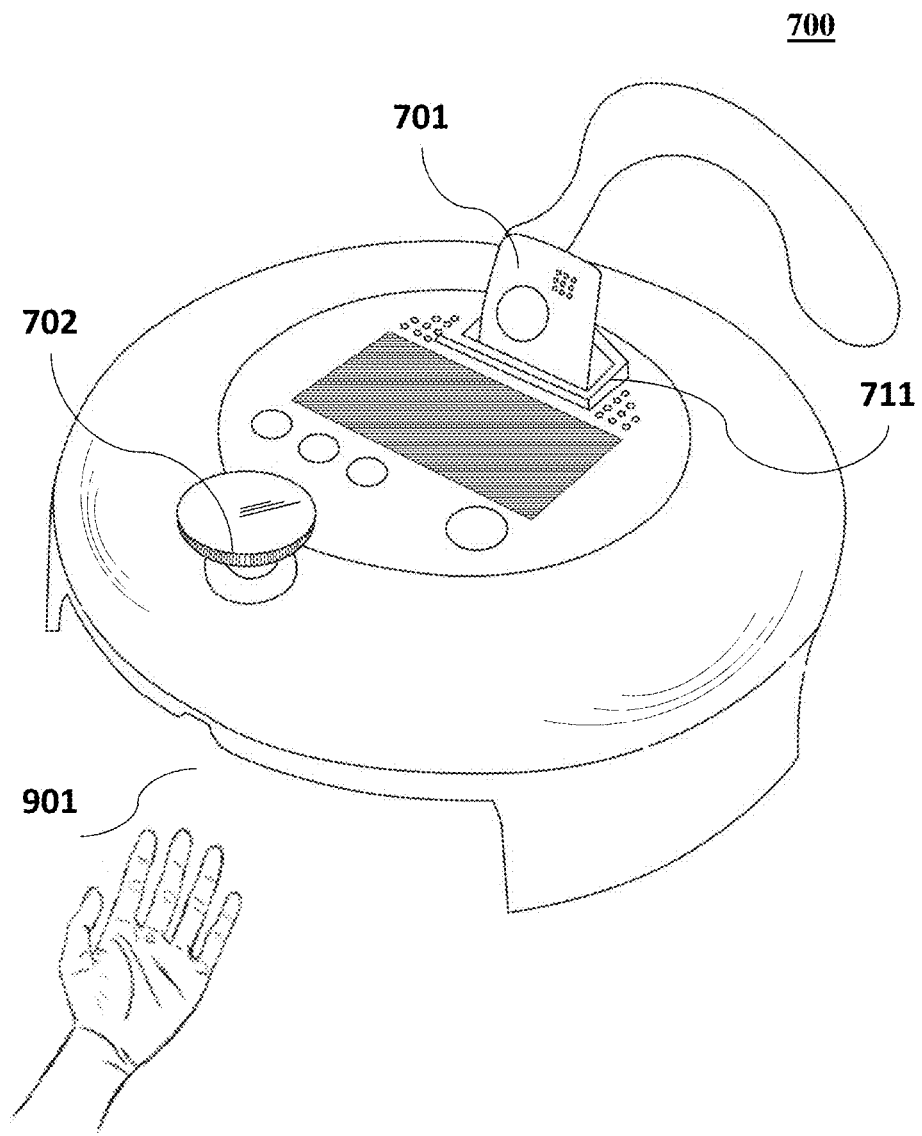
FIG. 9 is an illustration of the alternate embodiment of the present invention in use and further illustrating an optical photo sensor for automatic dispensing.

In FIGS. 9 and 10, there can be seen the dispensing of the medication 105, 106 by utilizing one or more optical and/or photo sensors 901 capable of detecting when an object, including the user's hand, has been placed under the medication egress 191 compartment.

FIG. 10 further illustrates a second embodiment for the bottom 350 of the present invention dispenser 100 containing one or more optical and/or photo sensors 901, which is capable of detecting when an object, including the user's hand, has been placed under the exit compartment 191 of the unit.

Figure 11:
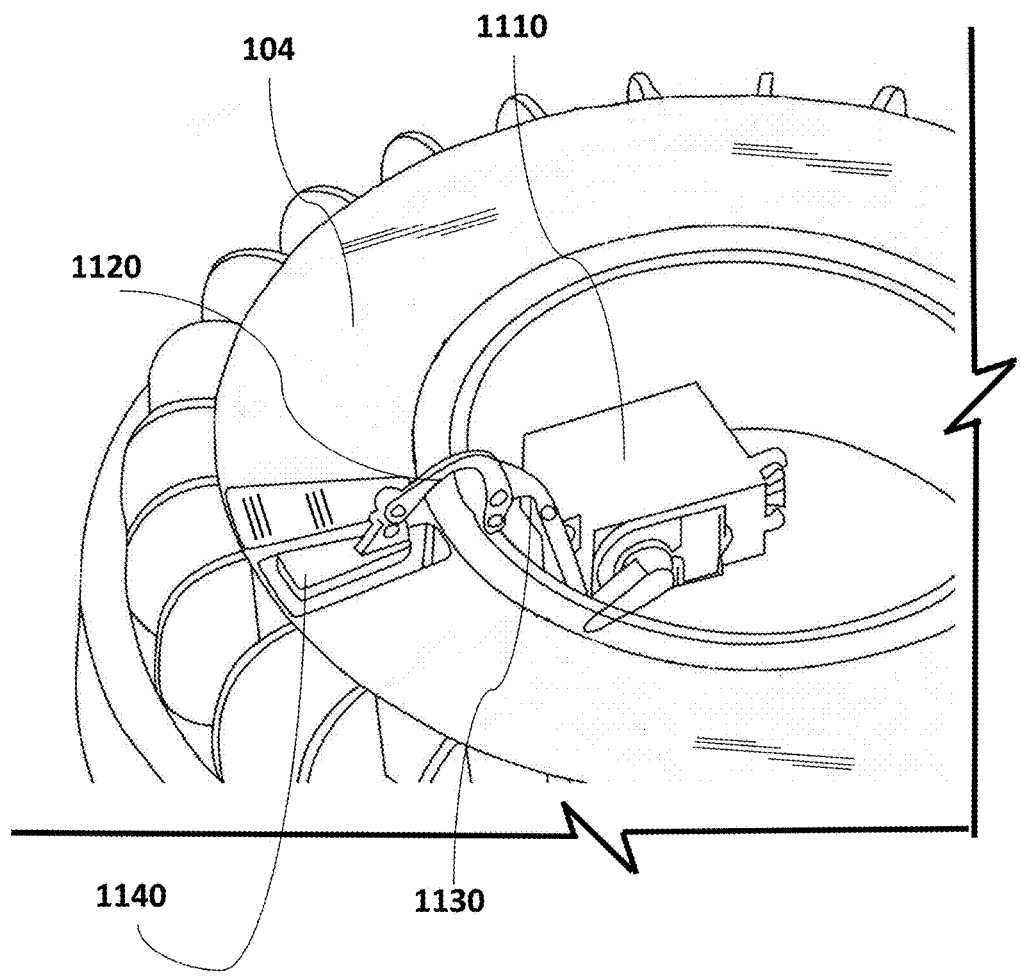
FIG. 11 is a detail of the dual arm, double-puncher in use during its first punch on a blister-pack to place medication into the carousel tray of the preferred embodiment of the present invention.
Figure 12:
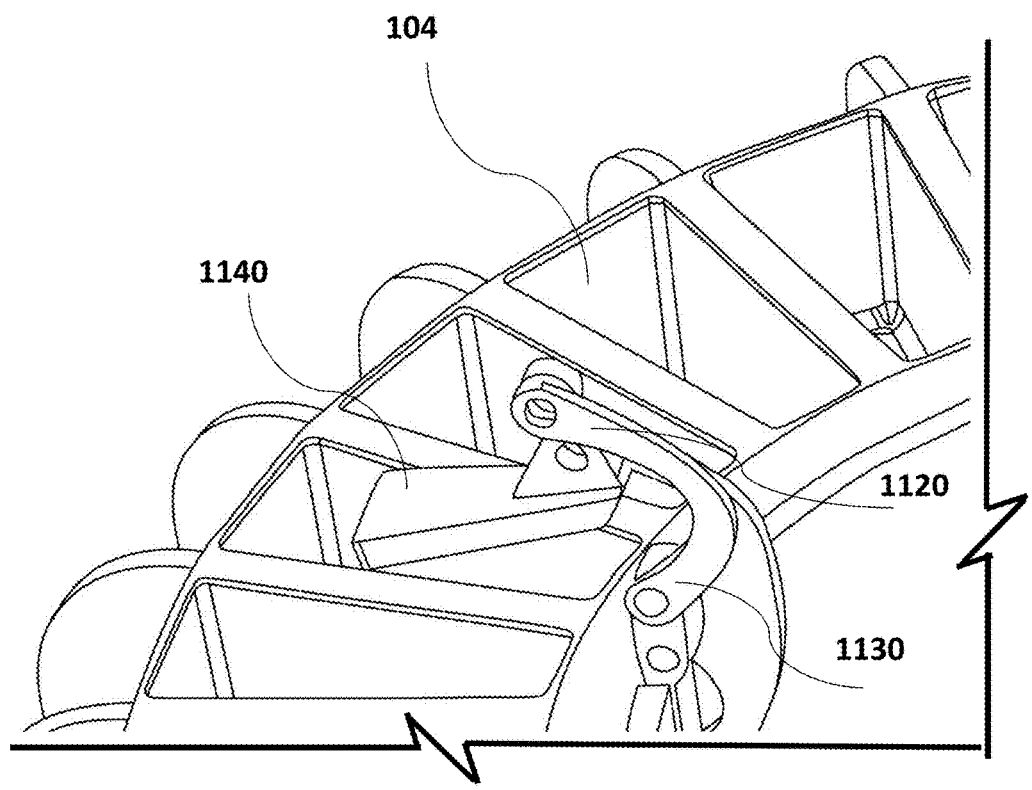
FIG. 12 is a detail of the motorized dual arm, actuation levers of the double-puncher in use on a blister pack of the preferred embodiment of the present invention.
Figure 13:
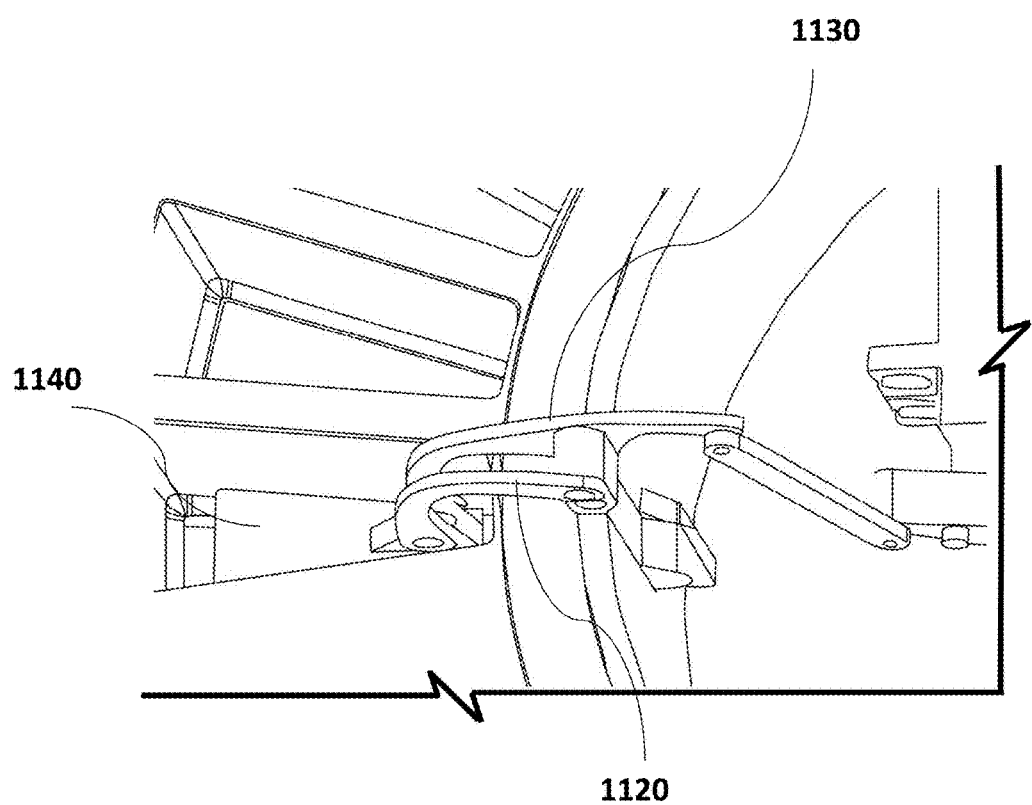
FIG. 13 is a detail of the motorized dual arm, double puncher in use on tis second punch to push the medication out of the blister pack in the preferred embodiment of the present invention.

In FIG. 11-13 there is shown an electronic mechanism 1140 for puncturing the blister pack 104 to dispense the contained medications 106. The unique and novel puncture mechanism 1140 utilizes a double armature having two separate shafts 1120 and 1130 to perform the appropriate motions to elevate, tilt and push down a lever 1140 on top of the blister pack 104 in order to provide the puncturing action for the pills 106 contained in each sealed compartment 162 of the blister pack 104. The unique double-puncturing system of the 1140 lever ensures all pills 106 contained in the appropriate compartment or pocket 162 of the blister pack 104 are properly released and fall down into the compartment 109 of the carousal tray 300. There is a first motion 1200 and a second motion 1300. As shown in FIG. 12, the first motion 1200 is performed in form of a quick tapping motion on the upper ceiling or circular top 161 of the blister pack 104 causing the punch lever 1140 to puncture the ceiling layer 161 of the blister pack 104. The curvature of arms 1120 and 1130 are such that lever 1140 is optimally positioned to perform this first motion 1200. As shown in detail in FIG. 13, the second motion 1300 is then performed in form of deep and slow press down action to ensure all pills 106 in the blister pack compartment or pocket 162 get pushed through the bottom layer of the blister-pack 163 and get released without incurring any damage. Again, the curvature of arms 1120 and 1130 are designed such that lever 1140 may reach into the interior of pocket 162 so as to fully and effectively push the medication 106 out of the blister pack and into the compartment 109 for dispensing during this second motion 1300.

FIG. 11 further shows the lever 1140 swung over on top of the blister pack 104 in flat position orientation due to the actions of the interaction of the two shafts 1120 and 1130. FIG. 12 shows the lever 1140 positioned on top 161 of the blister-pack 104 tilted in tilted position orientation due to the actions of the interaction of the two shafts 1120 and 1130. FIG. 13 further shows the lever 1140 having been pushed down through the upper ceiling or top of the blister pack 104 and further pressed down through the bottom floor 163 of the blister pack 104.

Figure 14A:
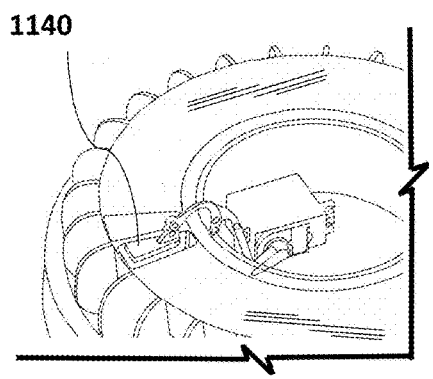
FIG. 14a is a detail of the automatic, motorized, dual arm, double puncher of the preferred embodiment of the present invention.
Figure 14B:
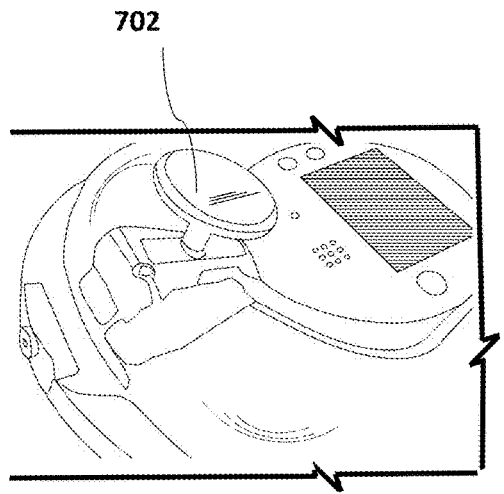
FIG. 14b is a detail of the manual puncher of the alternate embodiment of the present invention.

In FIG. 14 there is shown both the preferred embodiment and the second embodiment of the push lever. The Manual Push Lever (MPL) 702 is shown side-by-side with the Dual Press Motorized Lever (DPML) 1140.

Figures 15A, 15B:
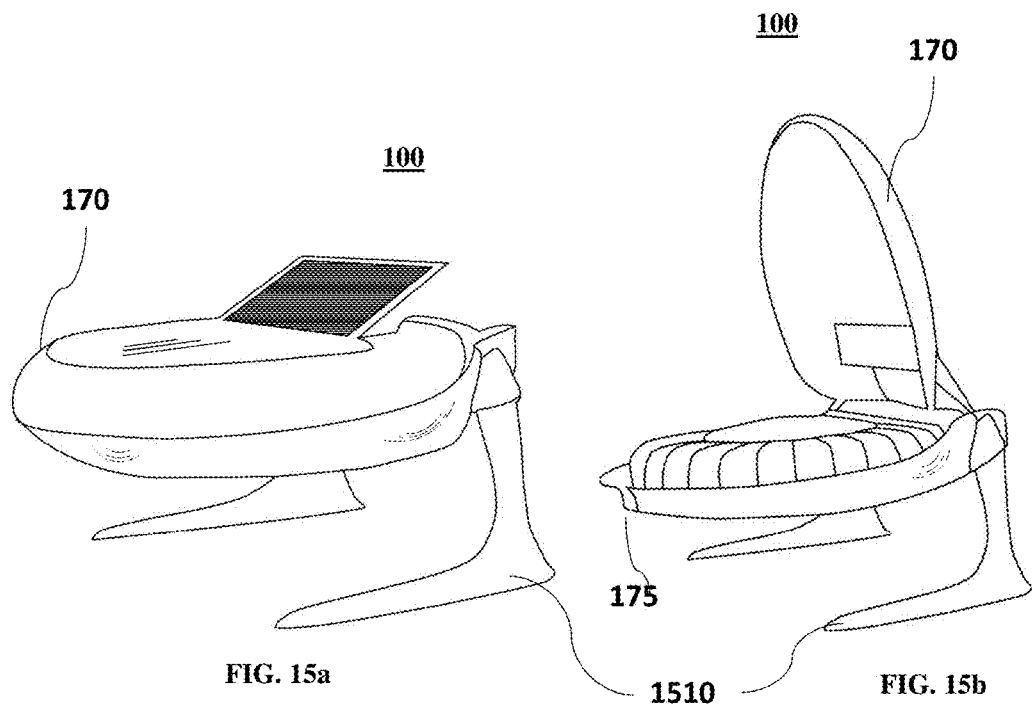
FIG. 15a is a side perspective view of a preferred embodiment of the present invention, shown with the top in the closed position.
FIG. 15b is a side perspective view of a preferred embodiment of the present invention, with the top open.
Figure 16:
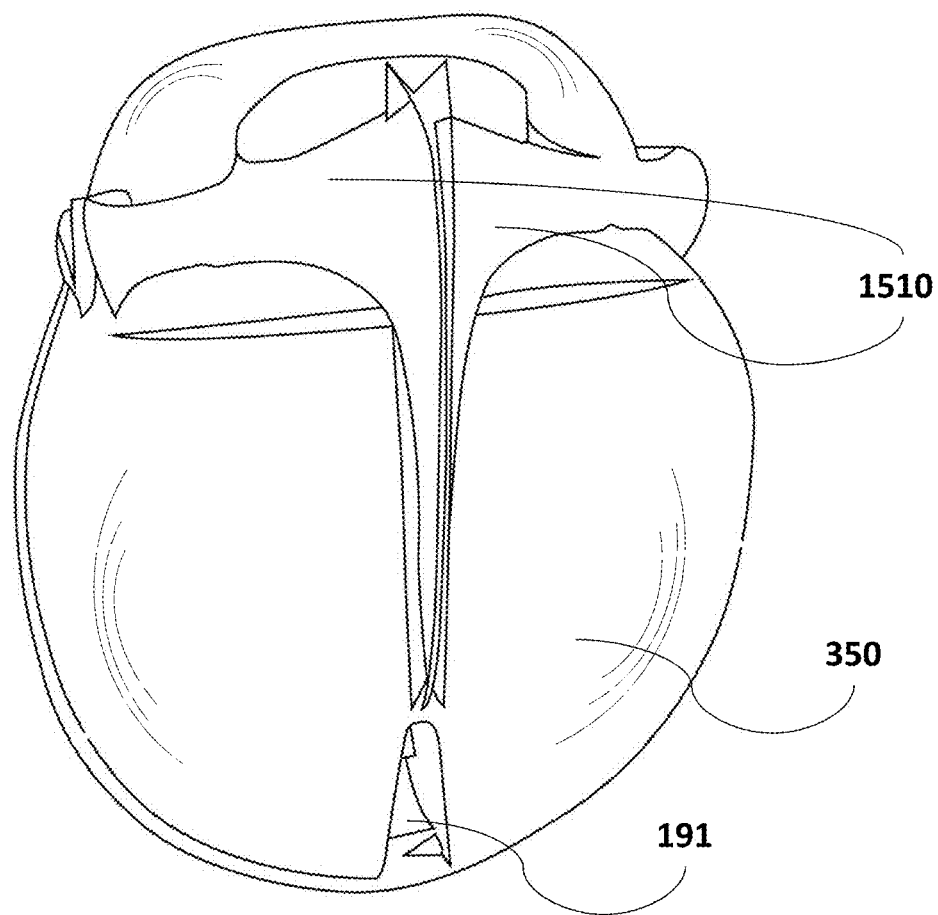
FIG. 16 is a bottom perspective view of the preferred embodiment of the present invention, further illustrating the retractable legs in the folded position.

Referring now to FIGS. 15 and 16, there is shown the unique foldable legs 1510. FIG. 15 illustrates the unique foldable legs 1510 of the present invention 100 in their extended position, and FIG. 16 shows the bottom view of the present invention dispenser 100 with the foldable legs 1510 in their folded-closed position.

Figure 17:
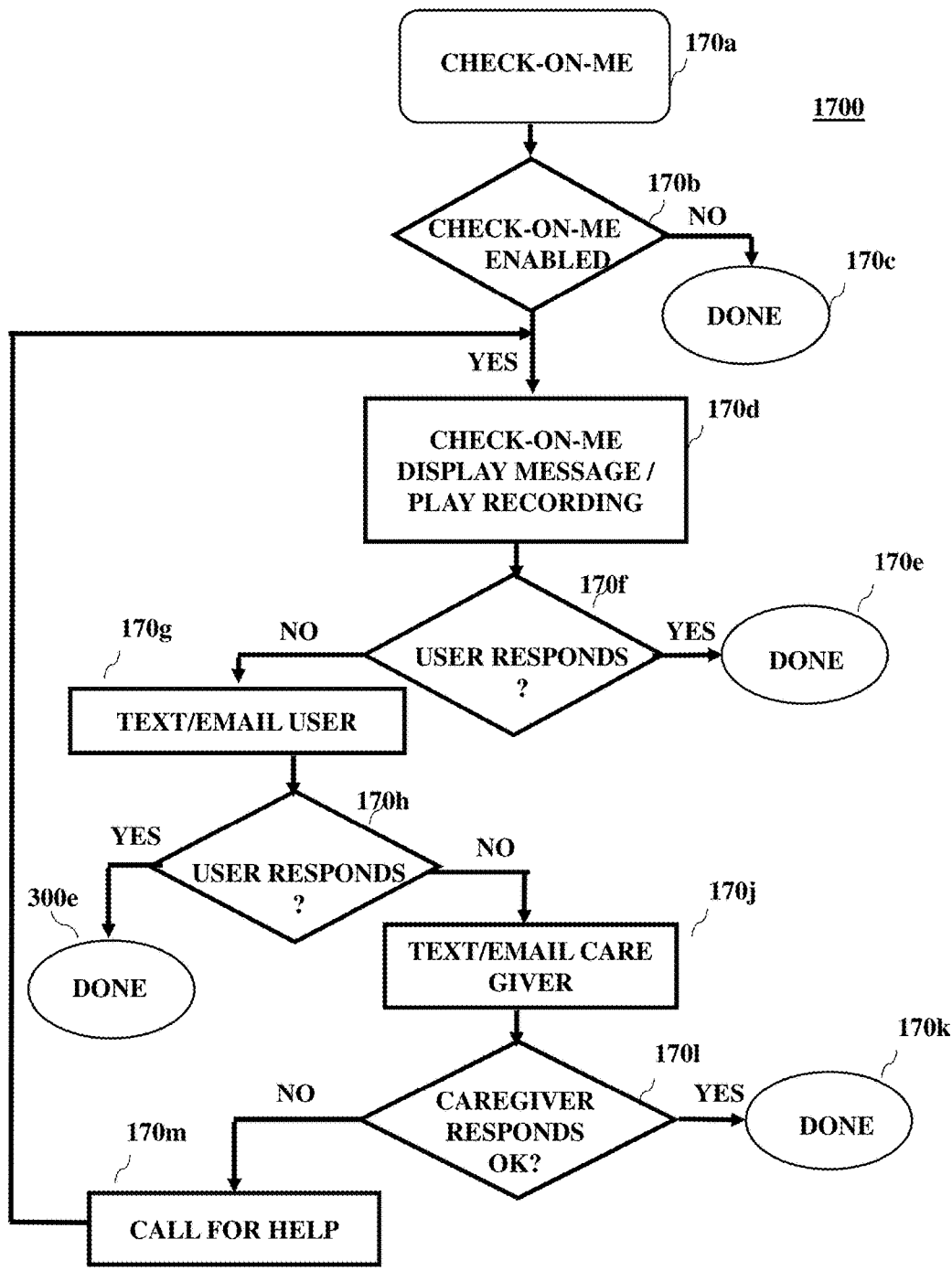
FIG. 17 is a flow diagram of a Check-On-Me feature of the preferred embodiment of the present invention.

Referring now to FIG. 17, there is shown the Contactless Automatic Pill Dispenser Check-On-Me process 1700. The Check-On-Me process 1700 begins with a continuous check as to whether the process is enabled 170b. If it is not, then the process is done 170c. If the process 1700 is enabled, then both display message 170d and call for help 170m are activated. If the user responds 170f to the display message 170d, then the process 1700 is complete. If the user doesn't respond 170f, then a text, email, or call is placed to the user 170g. If the user responds 170h at this point, then the process is done 300e. If the user hasn't responded 170h, then a text, email or call is placed to the caregiver 170j. The process then awaits a response from the care giver at 170. If the care giver responds, then the process 1700 is done 170k. If the care giver doesn't respond, then a call for help 170m is followed through to provide help and assistance to the patient who has been unable to respond.

Figure 18:
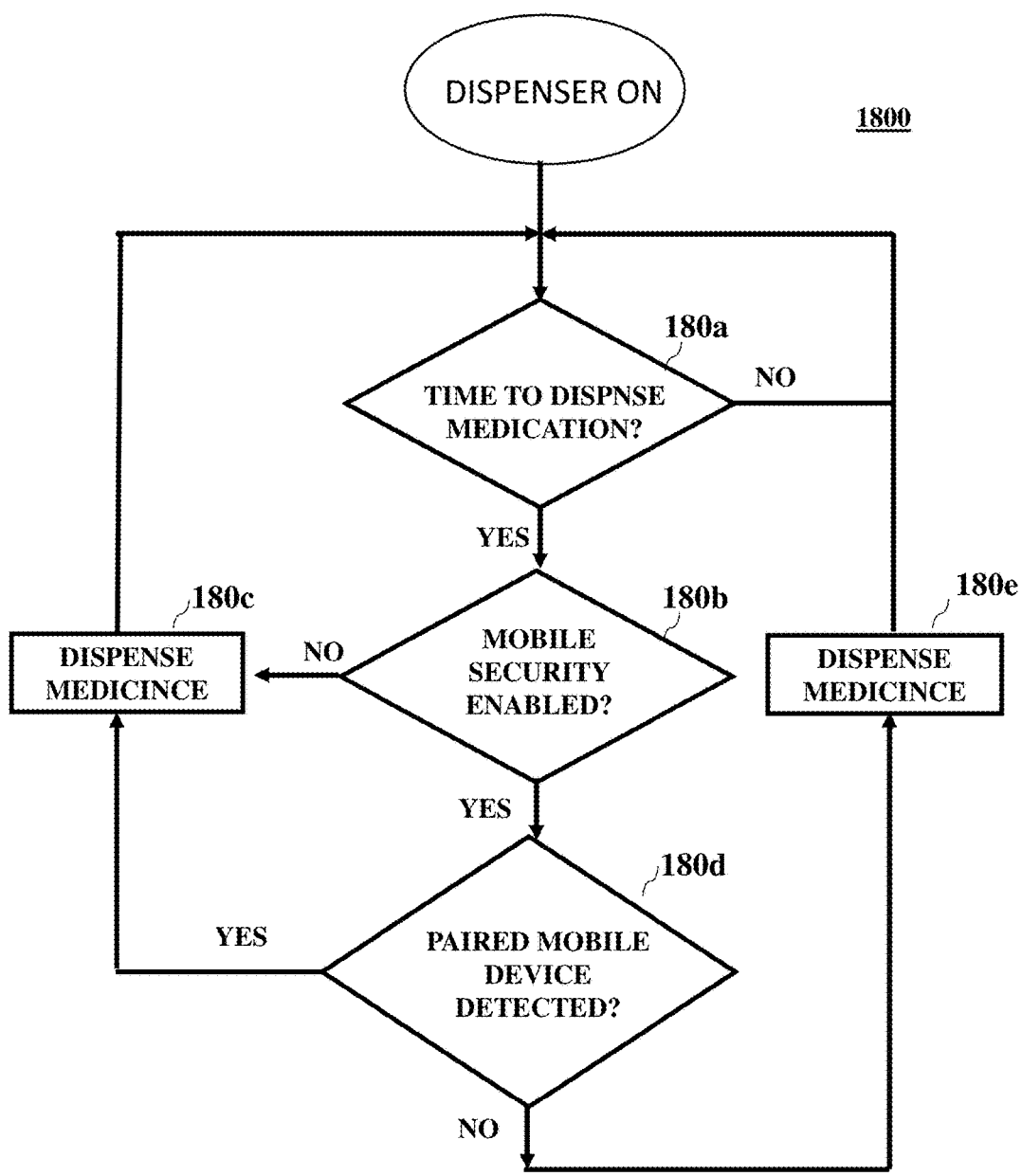
FIG. 18 is a flow diagram of a Secure Access feature of a preferred embodiment of the present invention.

Referring now to FIG. 18, there is shown the Contactless Automatic Pill Dispenser Mobile Secure Access process 1800. This process is a continual loop that begins when the dispenser 100 is turned on. The process 1800 begins its loop with checking whether it is time to dispense medication at 180a. If not, it goes back to the beginning of 180a, and continuously checks to see if it is time to dispense medication. If the answer to 180a is yes, then the process checks at 180b whether there is any security enabled. If there is no security enabled, then the process causes the dispenser 100 to dispense the medication at 180c. If there is a security enabled, then the process seeks out any paired devices at 180d. If there are no devices paired to the dispenser 100, then the dispenser 100 does not provide the medication at 180e and then begins the process all over again at 180a. If there is a paired device detected, then medication will be dispensed at 180c and the process will begin again from the beginning 180a.

Figure 19:
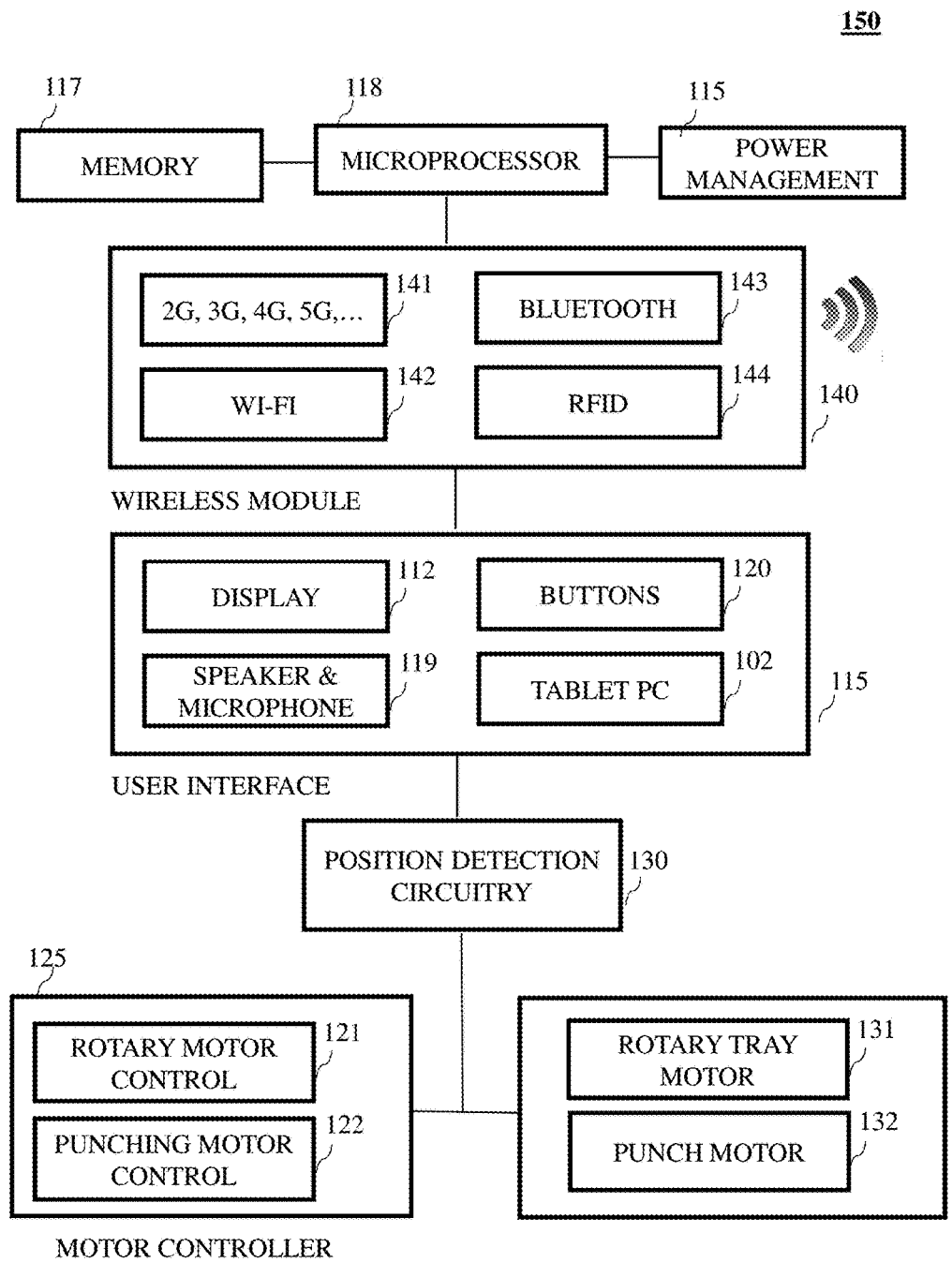
FIG. 19 is a block diagram of the electro-mechanical units and hardware architecture of the preferred embodiment of the present invention Contactless Automatic Pill Dispenser.

Referring now to FIG. 19, there is shown the Contactless Automatic Pill Dispenser Electro-Mechanical Control Unit block diagram. The present invention preferably includes a memory 117, a microprocessor 118, and a power management 115. The present invention also includes a wireless module 140 that may contain one or more of cellular communications 141, WI-FI 142, Bluetooth 143 or wireless Near Field Communication (NFC) or RFID 144 to detect and authenticate the presence of the authorized user before allowing for the medications 105, 106 to be dispensed. A user interface is also provided, preferably including at least a display 112, a speaker/microphone 119, input device 120 such as a button, and a computing device 102 such as a tablet or PC. The present invention further provides for a position detection 130, which detects the position of the available or appropriate carousel compartment 109 for dispensing. Referring back to FIG. 3, one device to make this determination is using a multiplicity of potentiometers 130 and a sensor as part of the position detection circuitry 130 to read the unique values at each location and associate it with each compartment 109. There is additionally provided a motor controller 125, which includes the rotary motor control 121 to control the rotary tray motor 131 and the punching motor control 122 which controls the punch motor 132.

The present invention dispenser 100 may further include a dual function optical sensing mechanism 901 to simultaneously provide a built-in barcode scanning functionality for scanning various barcodes including but not limited to medication bottles and prescriptions. The optical sensing mechanism further has the capability of detecting when an object, including the user's hand, has been placed under the exit compartment of the unit.

The dispenser 100 may provide for a lid 170 and a locking mechanism 175 for the lid 170 as shown in FIG. 15. The present invention may further include a Tamper Notification System (TNS). TNS provides for situations where if Locking Mechanism is opened or tampered with, notifications including but not limited to Text messages, emails, or phone calls, are sent to a designated set of persons, such as the authorized user and caregiver.

The present invention dispenser 100 may further utilize a unique Check-On-Me feature 1700, wherein the present invention dispenser 100 can be programmed to alert the user at various pre-scheduled times to press the unique Check-On-Me button to confirm the patient's status within a pre-programmed time interval. If the user fails to press the Check-On-Me button within the prescribed time limit, the dispenser 100 will alert remote operators of the user's lack of response. The Check-On-Me button may be in form of a physical button 120 on the dispenser 100 to be pressed, or it may be as an image on the touch display unit of the user interface 102 that upon being touched will perform the required action to notify the remote operator of the status of the user. This feature is particularly useful when it is deemed necessary to keep tabs on either a patient or on a caregiver, such as having an elderly patient check in periodically so that family members know that the patient was alright at a given time or may need help, or having a care giver check in to let others know that the care giver is present at the facility or house.

It is an object of the present invention to provide the ability for a user to insert and load sealed blister packs together with manual loaded pills simultaneously.

It is another object of the present invention to provide the ability for a user to simultaneously dual-dispense the medications by combining a motorized turning mechanism to simultaneously turn the carousal to dispense manually load pills along with a motorized punching mechanism to dispense the pills contained in the sealed compartment of the inserted blister pack.

It is yet another object of the present invention to provide the ability to use optical and/or photo sensor to allow for non-contact dispensing of medication using optical and/or photo sensor to allow for non-contact dispensing of medication.

It is yet another object of the present invention to provide access to various medication databases through the user interface 115 assist the caregiver as well as the actual user with information on the medication's usage and related side effects.

It is yet another object of the present invention to include wireless Near Field Communication (NFC) or RFID 144 to detect and authenticate the presence of the authorized user before allowing for the medications 105 and 106 to be dispensed It is yet another object of the present invention to provide for a dual function optical sensing mechanism to simultaneously provide a) a built-in barcode scanning functionality for scanning various barcodes including but not limited to medication bottles, prescriptions as well as b) detecting when an object, including but not limited to the User hand has been placed under the exit compartment of the unit.

What is claimed is:

1. A dispenser apparatus and system to dispense medication, to remind a user to take medication, including from a blister pack, to provide information to users, operators, and caregivers, and to track medication compliance, said users, operators, and caregivers having at least one hand, the dispenser comprising:
   a. a processor;
   b. a memory;
   c. a wireless transceiver, wherein said wireless transceiver includes a multiplicity of functions, including downloading a medication schedule;
   d. an interface display;
   e. a microphone;
   f. a speaker;
   g. a sensor mechanism, said sensor mechanism detecting when medication has been dispensed and providing notifications to a user via the interface display and the speaker, said sensor mechanism adapted to notify remote operators and caregivers via wireless communication when medication is dispensed;
   h. a rotatable carousel tray, said carousel tray having a multiplicity of compartments to contain and rotatably move medication as the carousel tray moves and having a keyed mechanism that provides for the carousel tray to be inserted in a specific position;
   i. a motorized mechanism to advance the rotatable carousel tray based on pre-loaded schedule;
   j. a medication ingress;
   k. a medication egress;
   l. a dispensing mechanism, wherein said dispensing mechanism retains and releases medication;
   m. a housing to contain the processor, the memory, the wireless transceiver, the display, the microphone, the speaker, the sensor mechanism, the rotatable carousel tray, the medication ingress, the medication egress, the dispensing mechanism;
   n. a dispense schedule, wherein said dispense schedule can be downloaded into the device both remotely or locally;
   o. a monitoring protocol, wherein said monitoring protocol monitors the download medication schedule, and is capable of notifying local operators and remote operators and caregivers, wirelessly in the event the operator fails to dispense the medication within the scheduled dispense time period;
   p. a Check-On-Me protocol, wherein said Check-On-Me protocol includes a non-detachable response device, such as a button, and wherein the device maybe programmed to alert the user at various pre-scheduled times to press the Check-On-Me button to confirm the user's status within a pre-programmed time interval, and further including an alert to remote operators if the user fails to press the Check-On-Me button;
   q. an accommodation for a blister pack of medication;
   r. a punching armature, said punching armature provides for the dispensing of medication from the blister pack such that medication that was manually placed in the dispenser and medication from a blister pack may be both dispensed from the dispenser;
   s. wherein said punching armature is motorized device; and
   t. wherein said punching armature further comprises a two-step, double punching mechanism, wherein the first punch punctures the blister pack, and the second punch gently pushes the medication into the carousel tray compartment.

2. The dispenser of claim 1 further comprising an optical non-contact sensor to detect a user's hand or a container into which the dispenser releases medication.

3. The dispenser of claim 1 further comprising a Manual Override mechanism to manually dispense medication.

4. The dispenser of claim 1 further comprising an RFID mechanism to detect and authorize a User before dispensing pills.

5. The dispenser of claim 1 further comprising a removable wireless panic button to alert and notify the User of device status and medication schedule when away from the pill dispenser.

6. The dispenser of claim 1, wherein the wireless transceiver pairs with one or more mobile devices thereby dispensing pills only when the paired mobile devices are within close proximity of and is authenticated by the pill dispenser.

7. A dispenser apparatus and system to dispense medication, including from a blister pack, to remind a user to take medication, to provide information to users, operators, and caregivers, and to track medication compliance, said users, operators, and caregivers having at least one hand, the dispenser comprising:
 a. a processor;
 b. a memory;
 c. a wireless transceiver, wherein said wireless transceiver includes a multiplicity of functions, including downloading a medication schedule;
 d. an interface display;
 e. a microphone;
 f. a speaker;
 g. a sensor mechanism, said sensor mechanism detecting when medication has been dispensed and providing notifications to a user via the interface display and the speaker, said sensor mechanism additionally able to notify remote operators and caregivers via wireless communication when medication is dispensed;
 h. a rotatable carousel tray, said carousel tray having a multiplicity of compartments to contain and rotatably move medication as the carousel tray moves and a keyed mechanism that provides for the carousel tray to be inserted in a specific position;
 i. a motorized mechanism to advance the rotatable carousel tray based on pre-loaded schedule;
 j. a medication ingress;
 k. a medication egress;
 l. a dispensing mechanism, wherein said dispensing mechanism retains and releases medication;
 m. a housing to contain the processor, the memory, the wireless transceiver, the display, the microphone, the speaker, the sensor mechanism, the rotatable carousel tray, the medication ingress, the medication egress, the dispensing mechanism;
 n. a dispense schedule, wherein said dispense schedule can be downloaded into the device both remotely or locally;
 o. a monitoring protocol, wherein said monitoring protocol monitors the download medication schedule, and is capable of notifying local operators and remote operators and caregivers, wirelessly in the event the operator fails to dispense the medication within the scheduled dispense time period;
 p. a Check-On-Me protocol, wherein said Check-On-Me protocol includes a response device, such as a button, and wherein the device maybe programmed to alert the user at various pre-scheduled times to press the Check-On-Me button to confirm the user's status within a pre-programs time interval, and further including an alert to remote operators if the user fails to press the Check-On-Me button;
 q. an optical non-contact sensor to detect a user's hand or a container into which the dispenser releases medication;
 r. an accommodation for a blister-pack; said accommodation residing within the housing;
 s. a punching armature, said punching armature providing for the dispensing of medication from a blister pack such that medication that was manually placed in the dispenser and medication from a blister pack may be both dispensed from the dispenser;
 t. wherein said punching armature is motorized device;
 u. wherein said punching armature further comprises a two-step, double punching mechanism, wherein the first punch punctures the blister pack, and the second punch gently pushes the medication into the carousel tray compartment; and
 v. wherein said first punching action consists of a fast tapping motion to puncture the top of the blister pack, and said second punching action consists of a slow and deep punching motion allowing the punching action to penetrate through both the top of the blister pack as well as the bottom layer of the blister pack, and wherein the second motion is further performed in form of slow press down force to ensure all pills in the blister pack compartment are dropped without incurring any damage.

8. The dispenser of claim 7, further comprising a Check-On-Me feature and button, where the device in claim 7, can be programmed to alert the user at various pre-scheduled times to press the unique Check-On-Me button to confirm their status within a pre-programs time interval and wherein if the user fails to press the Check-On-Me button, the device then alerts remote operators on users lack of response.

9. The dispenser of claim 7, using Manual Override mechanism to manually dispense medication.

10. A method and system to dispense medication, including from a blister pack, remind a user to take medication, provide information to users, operators, and caregivers, and track medication compliance, said users, operators, and caregivers having at least one hand, the method comprising:
 a. utilizing an automatic motorized pill dispenser for medication adherence and allowing individuals including caregivers to create a schedule for taking daily, weekly or monthly medication use at multiple intervals per day;
 b. providing the ability to program a time window for taking the said meditation at its proper time;
 c. downloading the schedule into an automatic medication dispensing device;
 d. rotating a carousal tray with multiple compartments, one compartment for each mediation intake time, utilizing a motorized mechanism;
 e. utilizing various sensors to indicate if and when medication was taken;
 f. monitoring the carousal tray position and various sensor readings at all times to alert the user when is time to take the medication; and
 g. utilizing wireless communication to notify remote operators such as a caregiver via text message, email or phone calls of when medications are taken;
 h. accommodating a blister pack;
 i. punching through said blister pack and dispensing said medication from the blister pack such that medication placed manually in the dispenser and medication from a blister pack may be simultaneously dispensed from the dispenser;
 j. electronically controlling said punching process; and
 k. said punching process further comprising the steps of puncturing the blister pack and pushing the medication into a compartment below.

11. The method of claim 10, further comprising the step of detecting and authenticating, by means of an optical non-contact sensor, a user's hand or a container into which the dispenser releases medication.

* * * * *